(12) United States Patent
Lewitus et al.

(10) Patent No.: US 10,160,831 B2
(45) Date of Patent: Dec. 25, 2018

(54) ASTAXANTHIN BASED POLYMER AND USES THEREOF

(71) Applicant: SHENKAR COLLEGE OF ENGINEERING AND DESIGN, Ramat Gan (IL)

(72) Inventors: Dan Lewitus, Herzliya (IL); Moran Fishman, Rehovot (IL)

(73) Assignee: Shenkar College of Engineering and Design, Ramat Gan (IL)

( * ) Notice: Subject to any disclaimer, the term of this patent is extended or adjusted under 35 U.S.C. 154(b) by 48 days.

(21) Appl. No.: 15/520,301

(22) PCT Filed: Oct. 19, 2015

(86) PCT No.: PCT/IL2015/051032
§ 371 (c)(1),
(2) Date: Apr. 19, 2017

(87) PCT Pub. No.: WO2016/063278
PCT Pub. Date: Apr. 28, 2016

(65) Prior Publication Data
US 2017/0327642 A1    Nov. 16, 2017

Related U.S. Application Data

(60) Provisional application No. 62/065,696, filed on Oct. 19, 2014.

(51) Int. Cl.
*C08G 65/34* (2006.01)
*C08G 63/553* (2006.01)
(Continued)

(52) U.S. Cl.
CPC .............. *C08G 65/34* (2013.01); *A61L 27/18* (2013.01); *A61L 27/34* (2013.01); *A61L 27/54* (2013.01); *A61L 29/06* (2013.01); *A61L 29/085* (2013.01); *A61L 29/16* (2013.01); *A61L 31/06* (2013.01); *A61L 31/10* (2013.01); *A61L 31/16* (2013.01); *C08G 63/54* (2013.01); *C08G 63/553* (2013.01); *C08G 63/676* (2013.01);
(Continued)

(58) Field of Classification Search
CPC .. C08G 65/34; C08G 63/553; C08G 65/3314; C08G 65/333; C08G 64/266; C08G 64/0291; C08G 63/676; C08G 63/54; A61L 31/16; A61L 61/06; A61L 27/18; A61L 27/34; A61L 27/54; A61L 31/10; A61L 29/085; A61L 29/16; A61L 29/06; A61L 2420/02; A61L 2300/404
See application file for complete search history.

(56) References Cited

U.S. PATENT DOCUMENTS

2009/0319031 A1    12/2009  Wang et al.

FOREIGN PATENT DOCUMENTS

WO    03/066583 A1    8/2003
WO    2004/011423 A2    2/2004

OTHER PUBLICATIONS

Middleton et al., "Organocatalytic synthesis of astaxanthin-containing poly(lactide)s", Polym. Chem., vol. 2, pp. 595-600, (2011).

*Primary Examiner* — Trevor Love
(74) *Attorney, Agent, or Firm* — Vorys, Sater, Seymour & Pease LLP

(57) ABSTRACT

Provided are polymers having a repeating unit including at least one astaxanthin moiety. Also provided are processes for preparing the polymers and various uses thereof.

14 Claims, 13 Drawing Sheets

(51) Int. Cl.
  *C08G 65/331* (2006.01)
  *C08G 65/333* (2006.01)
  *A61L 31/16* (2006.01)
  *A61L 31/06* (2006.01)
  *A61L 27/18* (2006.01)
  *A61L 27/34* (2006.01)
  *A61L 27/54* (2006.01)
  *A61L 31/10* (2006.01)
  *A61L 29/08* (2006.01)
  *A61L 29/16* (2006.01)
  *A61L 29/06* (2006.01)
  *C08G 64/26* (2006.01)
  *C08G 64/02* (2006.01)
  *C08G 63/676* (2006.01)
  *C08G 63/54* (2006.01)

(52) U.S. Cl.
  CPC ....... *C08G 64/0291* (2013.01); *C08G 64/266* (2013.01); *C08G 65/333* (2013.01); *C08G 65/3314* (2013.01); *A61L 2300/404* (2013.01); *A61L 2420/02* (2013.01)

| Positions | 1H NMR d (500MHz, CDC13) H | C |
|---|---|---|
| 25, 26, 43, 44 | 1.24 and 1.37 each 6H | 26.52, 30.76 |
| 50, 51 | 1.44 4H | 28.9 |
| 49, 52 | 1.73 4H | 24.93 |
| 28, 40 | 1.91 6H | 14.23 |
| 30, 31, 32, 33 | 2.00 and 2.01 each 6H | 12.72, 12.95 |
| 21, 36 | 2.06-2.09 4H | 42.81 |
| 53, 47 | 2.46 | 34.33 |
| 22, 37 | 5.55 | 70.99 |
| 1,2,4,5,6,8,9,10,11, 13,14,15,17,18 | 6.20-6.69 14H | 123.33, 124.74, 130.79, 133.92, 135.19, 139.78, 142.33 |
| 20, 35 | | 37.24 |
| 24, 39 | | 128.47 |
| 3,7,12,16 | | 136.28, 134.68 |
| 34, 19 | | 160.68 |
| 46 | | 173.28 |
| 23, 38 | | 194.33 |

ASTAXANTHIN BASED POLYMER AND USES THEREOF

TECHNOLOGICAL FIELD

The present disclosure generally relates to polymers having a monomeric repeating unit comprising astaxanthin (ATX) moiety and uses thereof.

BACKGROUND

Astaxanthin (3,3'-dihydroxy-β,β carotene-4,4'-dione, ATX) is an organic red pigment belonging to the xanthophyll family (oxygenated carotenoids), containing both hydroxyl and ketone functional groups. ATX possesses the empiric formula of ($C_{40}H_{52}O_4$) and is produced by microorganism such as fungi and alga, and is currently used as a health/nutritional food supplement.

ATX has self-limited absorption orally, antibacterial properties and antithrombotic properties in various animal models. ATX is a potent antioxidant, and may be beneficial in cardiovascular, immune, inflammatory and neurodegenerative diseases.

Implantable medical devices, such as heart valves, prosthetic joints and intravascular catheters, are at risk of becoming a source of infection via surface-adhering bacteria. As the lumen of the device is coated by microorganisms, nutrient rich blood products provide ideal growth niche for bacteria as it passes through or around the device. Microorganisms become embedded on the device to form thereon a biofilm resistant to conventional antimicrobial treatments. Biofilm formation leads to the development of a fibrin sheath, infection and thrombus formation.

The requirements of medical devices include: 1) biocompatibility; 2) strong evidence of anti-infective efficiency; 3) fixation and durability; and 4) mechanical characteristics that match the application. Further, medical devices such as a dialysis catheter should additionally prevent thrombus and fibrin sheath formation; and provide a broad-spectrum antimicrobial activity. Thus, antibacterial and antithrombotic coating for medical devices is needed.

Middleton et al. (*Organocatalytic synthesis of astaxanthin-containing ploy(lactide)s, Polym. Chem.*, 2011, 2, 595-600A), describe the synthesis of astaxanthin-containing poly (lactide)s by the ring-opening polymerization of lactide initiated from residual alcohol groups on astaxanthin using a thiourea/tertiary amine catalyst. The astaxanthin was used as a catalyst for the reaction, and as such remained in relatively small quantities in the poly(lactic acid) chains prepared, compared to the amount of lactic acid therein. Low molecular weight polylactides of up to 30 kD Mw were synthesized, where the higher molecular weight polymers led to smaller content of astaxanthin catalyst (210 lactide molecules to one ATX). Additionally, the reaction times were several days, which is commercially impractical.

The use of ATX in clinical applications is limited, mainly to oral application, which, while providing a systemic effect, is not sufficient to treat certain localized conditions, and further, since it has only immediate release effects, it does not provide a desired controlled release treatment, which would enable the treatment of various conditions.

The polyastaxanthin based polymers disclosed herein represent a significant technological step from the astaxanthin-based polymers known in the art. One of the drawbacks of ATX-containing polymers known in the field is that such polymers comprise only a single ATX unit. For example, astaxanthin-containing polylactide is a polymer that comprises polylactide, ($-C_3H_4O_2-)_n$, as the repeating unit and a single ATX unit.

Acknowledgement of the above references herein is not to be inferred as meaning that these are in any way relevant to the patentability of the presently disclosed subject matter.

GENERAL DESCRIPTION

The present disclosure is directed to polymeric materials wherein the monomeric repeating unit in said polymer comprises at least one ATX moiety. The polymers of the present disclosure have varying chemical and physical properties making them suitable for various medical uses.

Astaxanthin is a compound known to have potent bioactivity, including: antioxidant, antibacterial, antithrombotic and anticancer properties. However, the implementation of ATX-compound in clinical applications was shown to be limited due to insufficient controlled release effects.

Thus, a primary objective of the present disclosure is to provide a polymer having a monomeric repeating unit comprising ATX moiety that at least maintains the bioactivity properties that originate from the ATX component and also utilizes the advantages of the polymeric form for various needs. A further objective of the present disclosure is to provide a polymer with enhanced overall bioactivity relative to the bioactivity of the ATX compound.

Thus, in its first aspect, the disclosure provides a polymer having a repeating unit comprising at least one Astaxanthin moiety.

In a second of its aspects, the disclosure provides a polymer having the following repeating unit -$[ATX]_n$- wherein ATX is an astaxanthin moiety and n is an integer being at least 2 indicating that the repeating unit is repeated in the polymer of the invention at least twice.

In the context of the present disclosure, the term "repeating unit" denotes the basic monomeric unit that is repeated at least twice to form a polymer of the disclosure. The monomeric units of a polymer of the disclosure are connected to each other via any chemical bond or association known in the field of the invention (such as for example covalent bond, hydrogen bond, pi-pi stacking, complex bond, coordination bond and so forth).

The repeating unit of the polymer of the invention comprises at least one ATX moiety having at least one of the valancies of the ATX molecule dedicated to a bond to at least one unit of the polymer of the invention. In some embodiments, the repeating unit is -$[ATX]_n$-, wherein n is 2 or higher. In some further embodiments, n is an integer between 2 and 2000000.

As used herein, the term "polymer" denotes a synthetic branched or straight macromolecule that comprises at least two repeating units as defined hereinabove. In some embodiments, said polymer of the invention is a homopolymer, i.e. all the repeating unit are similar. In some other embodiments, the polymer of the invention is a heteropolymer, i.e. it is formed by at least two different repeating units, at least one of which comprises ATX. In some further embodiments a polymer of the invention is a co-polymer, i.e., it is formed by at least two different polymers (said difference being any type of difference including different repeating units, different connectivity of the repeating units, different cross linking and so forth), at least one of which comprises in its repeating unit at least one ATX moiety. It should be noted that a polymer of the invention may include different or similar end moieties (located at the end of the polymer chains).

Thus in a further aspect, the present disclosure provides a copolymer comprising at least one polymer associated (via any type of association including a chemical bond, electronic interaction bond and so forth) with at least one other polymer.

In some embodiments the repeating unit of a polymer of the invention further comprises at least one other moiety. Said at least one other moiety is connected to the ATX moiety via any type of bond known in the field, such as for example chemical bond, electrical interaction bond, metal association bond and so forth. Under such embodiments a polymer of the invention can be selected from the following repeating units -[ATX-M]$_n$- (i.e. ATX is bonded to moiety M which bonds to the next repeating unit), -[ATX(M)]$_n$- (i.e. ATX is bonded to moiety M. ATX bonds to the next repeating unit), -[M(ATX)]$_n$- (i.e. M is bonded to moiety ATX. M bonds to the next repeating unit), wherein ATX is an astaxanthin moiety, M is a further moiety, and n is an integer being at least 2 indicating that the repeating unit is repeated in the polymer of the invention at least twice. In some further embodiments, a polymer of the invention may comprise at least two other moieties being the same or different.

When polymerizing astaxanthin monomer with at least one other moiety, including: a comonomer, oligomer and polymer; an astaxanthin based polymer (ATX-based polymer) is obtained. Examples for such at least one other moiety includes, but are not limited to ethylene glycol, polyethylene glycol, suberic acid, diacid, diol, diisocyanate or any functional group that can react with a diol group, wherein its backbone comprises one or more carbons connected via an alkane, alkene, ether, ester, amine, amide, peptide, urea, urethane, anhydride or carbonate bonds.

The properties of the astaxanthin based polymer provided herein can be tailored in accordance with the properties of said at least one other moiety, including but not limited to: mechanical properties, such as, Young's modulus, strength, toughness, flexibility; and chemical and physical properties, such as, hydrophobicity, hydrophilicity and erosion rate. For example, the experimental results shown herein (particularly the in vitro degradation studies in phosphate buffer saline at 37° C. shown below) exhibit that some of the ATX polymers provided herein degrade via bulk erosion and some through surface erosion, depending on the chemical structure of the at least one other moiety.

As appreciated, the ATX compound is a bioactive compound. The bioactivity of the ATX based polymer disclosed herein results at least from the bioactivity of the ATX moiety in the polymer. The at least one other moiety can further contribute additional bioactivity properties to the ATX-based polymer.

In some embodiments of the present invention said at least one other moiety is selected from a bioactive moiety (i.e. said at least one other moiety in the repeating unit provides additional bioactivity on top of the bioactivity of said ATX moiety), a biocompatible moiety (i.e. said at least one other moiety in the repeating unit provides biocompatible properties making the end polymer able to perform with an appropriate host response in a specific biological situation), hydrophobic moiety (i.e. said at least one other moiety in the repeating unit provides hydrophobic properties to the end polymer), hydrophilic moiety (i.e. said at least one other moiety in the repeating unit provides hydrophilic properties to the end polymer), or any combinations thereof.

Thus, in some embodiments, the at least one other moiety, being one or more of bioactive and biocompatible. In some embodiments, the at least one other moiety, being bioactive.

As appreciated, the at least one other moiety of a polymer of the disclosure provides the end polymer with at least one of mechanical stability, thermal stability, chemical stability or microbial stability or any combinations thereof. Such properties are designed in accordance with the end use of a polymer of the invention and its intended utility.

When referring to "mechanical stability" it is to be understood as referring to stability or lack of detectable change over a prolonged period of time (or at least over the designated storage and use period of a polymer of the invention) in terms of mechanical properties of the polymer, including but not limited to, Young's modulus, flexural modulus, toughness, hardness, tensile strength, elongation at break, viscosity, etc. all designed in accordance with the utility and use of the polymer of the invention in the designated purpose.

When referring to "chemical stability" it is to be understood as referring to the polymers substantial resistance to decomposition of the polymer at any one of a temperature range of 0 to 100° C. and pH range of 3 to 10. For instance, the polymer provided in Example 2 below exhibited chemical stability at a temperature of 37° C. in a solution with pH of 7.4 for at least 30 days, with 5% weight loss was observed. At times, the polymer provided herein exhibited chemical stability at a temperature of 37° C. in a solution with pH of 7.4 for at least 1, 2, 3 and 4 weeks, with at most 5%, 10%, 20% and 30% weight loss. All designed in accordance with the utility and use of the polymer of the invention in the designated purpose.

When referring to "microbial stability" it is to be understood as referring to inhibiting or slowing the progress of development of detectable colony growth associated with the polymer or maintenance (lack of increase) in the number of colony forming units associated with the polymer at a temperature of 37° C. At times, throughout the disclosure herein, the polymer of the present disclosure is regarded as being anti-bacterial, i.e., the polymer inhibits the growth and biofilm formation of bacteria. All designed in accordance with the utility and use of the polymer of the invention in the designated purpose.

For instance, the experimental results provided herein exhibit the antibacterial properties of the ATX polymer disclosed herein against at least three different microorganisms: *Staphylococcus aureus* MRSA252, *S. aureus* MSSA476 and *S. epidermidis* 1457, at 37° C. As appreciated, the ATX polymer provided herein is effective in inhibiting the growth and biofilm formation of bacteria. Thus, the ATX polymer can be applied as a coating for medical devices, including catheters and other implantable medical devices.

When referring to "thermal stability" it is to be understood as encompass the ability of a polymer of the invention to withstand predetermined temperature changes (either in storage or while being put to use), in accordance with the utility of a product comprising a polymer of the invention, substantially resisting decomposition.

In some embodiments, the at least one other moiety provides at least one of mechanical, thermal, microbial and chemical stability to the polymer.

In some embodiments, the at least one other moiety is a polymer. In such embodiments, the polymer is a poly (ethylene glycol) (referred herein: "PEG") or any derivative thereof. In some embodiments the PEG is poly(ethylene glycol)bis(carboxymethyl)ether or any derivative thereof.

In some embodiments the at least one other moiety is selected from selected from a carboxylic acid moiety, an anhydride moiety, an epoxide moiety, an acyl moiety, a phosgene derivative, an isocyanate moiety or any combinations thereof. In such embodiments, the carboxylic acids are selected from any one of hexadecanoic acid, sebacic acid, suberic acid, dodecanedioic acid and any combinations thereof. In some embodiments, the polymer disclosed herein is a copolymer comprising at least one ATX moiety, at least one carboxylic acid moiety (for example, sebacic acid) and at least one polymeric moiety (for example, PEG).

As noted above, the properties of the polymer disclosed herein varies with the type of moieties used and the polymerization conditions. One of these properties is the hydrophobicity or hydrophilicity of the polymer. Thus, in some embodiments, the polymer being a hydrophobic or hydrophilic polymer. In some other embodiments, the polymer disclosed herein comprising at least one of a hydrophobic moiety and a hydrophilic moiety.

A further property is the average molecular weight in terms of "mass average molar weight" (i.e., Mw) of the polymer disclosed herein, which influences the mechanical and thermal properties of the polymer. In some embodiments, the polymer disclosed herein having a Mw of at least 15 kDa, at times, at least 20 kDa, at times at least 25 kDa, at times at least 30 kDa, at times, at least 35 kDa, at times at least 40 kDa, at times, at least 45 kDa, at times at least 50 kDa, at times at least 55 kDa, at times at least 60 kDa, at times at least 65 kDa and yet further at times, at least 70 kDa, at least 100 kDa, at least 200 kDa, at least 300 kDa. In some embodiments, the polymer disclosed herein having Mw between about 15 to 120 kDa, at times between about 15 to 300 kDa, at times between about 15 to 200 kDa, at times between about 15 to 100 kDa, between about 15 to 80 kDa, between about 15 to 60 kDa, between about 15 to 50 kDa, between about 15 to 45 kDa, between about 15 to 40 kDa and between about 15 to 35 kDa. In some embodiments, the polymer disclosed herein having a Mw between about 25 to 110 kDa, at times between, about 25 to 90 kDa, between about 25 to 70 kDa, between about 25 to 60 kDa, between about 25 to 55 kDa, between about 25 to 50 kDa, between about 25 to 45 kDa. In some embodiments, the polymer disclosed herein having a Mw between about 30 to 110 kDa, at times between, about 30 to 90 kDa, between about 30 to 70 kDa, between about 30 to 60 kDa, between about 30 to 55 kDa, between about 30 to 50 kDa and between about 30 to 45 kDa.

In some embodiments, the polymer disclosed herein having Mw between at least any one of: 15 kDa, 25 kDa, 30 kDa, 90 kDa, 35 KDa, 40 KDa, 45 KDa, 50 KDa or 55 KDa; to at most any one of: 300 kDa, 250 kDa, 200 kDa, 120 kDa, 110 kDa, 100 kDa, 90 kDa, 80 KDa, 70 KDa, 60 KDa, 50 KDa or 40 KDa.

As appreciated, the polymer disclosed herein comprises a significant amount of ATX. In some embodiments, the polymer disclosed herein comprises at least about 10% w/w ATX, at times at least about 15% w/w ATX, at times, at least about any one of 20%, 25%, 30%, 35%, 40%, 45%, 50%, 55%, 60%, 65%, 70%, 75%, 80% and 85% w/w, and even further at times the polymer disclosed herein comprises at least about 90% w/w ATX.

In some embodiments, the polymer disclosed herein comprises ATX in the range of at least about 10%, 20%, 30%, 40%, 50%, 60%, 65%, 70%, 75% or 80% w/w; to at most about 90%, 85%, 80%, 70%, 60%, 50%, 40%, 30% or 20% w/w.

Yet further, in some embodiments, the polymer disclosed herein comprises at least about 10%, 20%, 25%, 30%, 35%, 40%, 45%, 50%, 55%, 60%, 65%, 70%, 75%, 80% or 85% w/w ATX, and has a Mw of at least about any one of 15 kDa, 25 kDa, 30 kDa, 90 kDa, 35 KDa, 40 KDa, 45 KDa, 50 KDa or 55 KDa.

In some embodiments, the polymer disclosed herein exhibits a glass transition temperature ("Tg") ranging from 10° C. for a polymer comprising flexible molecules such as ethylene glycol, to 150° C. for polymers comprising rigid backbones such as terephthalatic acid. Such polymer exhibits Young's modulus in the range of 100-2000 MPa.

The term "glass transition temperature", Tg, denotes the threshold temperature above which a polymer transforms from an amorphous rigid state to a more flexible state, also referred as the rubber phase. As the temperature decreases below the Tg, the polymer becomes more brittle, also referred as the glass phase. Thus, information regarding the Tg of a polymer is essential in the selection of polymeric materials for various applications. The polymer of the present disclosure can be tailored as a function of the nature of the at least one other moiety, the molecular weight and distribution of the polymer, the synthesis conditions, synthesis precursors, etc. For example, if strong physical properties (against compression, tension, shear) of the material is required when it is being used at a certain temperature, this requires using a polymer in the rigid, glassy state at a temperature below the Tg. In this case, a glassy polymer is formed by long chains, networks of linked atoms or a complex molecular structure.

In other embodiments, the glass transition temperature, Tg, ranges from 20 to 100° C., at times from 30 to 100° C., and further at times from 40 to 100° C.; at times from 20 to 80° C., at times from 30 to 80° C., at times from 40 to 80° C., and further at times from 50 to 80° C.; at times from 20 to 70° C., at times from 30 to 70° C., at times from 40 to 70° C., at times from 50 to 70° C.

When the polymer disclosed herein comprises high amount of hydrophilic moieties, said polymer can be fabricated into a cross-linked hydrogel (i.e., network of polymer chains that are hydrophilic). Such polymer exhibits Young's modulus in the range of 10-100 kPa when hydrated. Thus, in some embodiments, the polymer disclosed herein having Young's modulus in the range of 10-100 kPa.

In some embodiments, the Young's modulus at 0-70° C. is in the range of at least 10 kPa, 100 kPa, 400 kPa, 500 kPa, 700 kPa, 1 MPa, 100 MPa, 200 MPa, 300 MPa, 400 MPa, 500 MPa, 600 MPa, 700 MPa, 800 MPa, 900 MPa, 1000 MPa, 1100 MPa or 1200 MPa; to at most 2000 MPa, 1700 MPa, 1500 MPa, 1300 MPa, 1200 MPa, 1000 MPa, 900 MPa, 800 MPa, 700 MPa, 600 MPa, 500 MPa, 400 MPa, 300 MPa, 200 MPa or 100 MPa.

Without being bound by theory, the ATX compound is considered to have insufficient controlled release effects, thus its implementation in clinical applications is limited. In order to elucidate the release mechanism of the ATX moiety, the erosion mechanism (both bulk and surface) was tested and the hydrophobicity of the at least one other moiety was measured.

Thus, in some embodiments, the polymer disclosed herein having an erosion rate (measure as mass loss from the bulk polymer, as in degradation studies as stated above) of between about 24 hours to about 24 months, at times between 24 hours to 12 months, at times between 24 hours to 5 months. The erosion rate property can be used in order to determine the release mechanism of the ATX moiety.

In the context of the present disclosure, the term "controllably releasing" denotes the delivery of at least one active compound in response to stimuli or time, including time dependent release, sustained release, pulse release, delayed release, etc, to maintain drug levels within the therapeutic window and to maximize therapeutic efficiency. The ATX release rate can depend on the surrounding conditions, including, temperature, pH, fluid circulation rate, implant site, sterilization conditions, molecular weight, humidity, pressure, etc. The release rate can depend on the amount of ATX in the polymer. The release rate can also depend on the molar weight distribution, the molar weight average, the structure of the polymer (co-monomer content, linearity, hydrophobicity, etc.), the amount of impurities, etc. In some embodiments, the polymer disclosed herein being capable of controllably releasing ATX.

In yet some embodiments, the polymer disclosed herein, at least partially retains the ATX moiety therapeutic properties, and thus, even without degradation, the polymer will provide certain medical and/or therapeutic properties.

In some embodiments, the polymer can contain therein effective amounts of ATX moiety, which is capable of being released over a certain and predetermined period of time. In addition, the polymer can further contain therein effective amounts of an additional other active moiety having therapeutic properties, including, anti-infective, anti-inflammatory, anti-cancerous, etc, to thereby provide additional therapeutic effect to the polymer.

In some embodiments, the polymer described herein being at least one of biocompatible, anti-inflammatory, antioxidant, anticancer, antibacterial and antithrombotic.

The term "biodegradable" in the context of the polymer of the present disclosure, is denoted as a polymer that is capable of being at least partially or at some instances fully, decomposed by bacteria or other living organisms/microorganisms. Since the polymer of the present disclosure can be biodegradable, when degraded, it is capable of releasing ATX molecules into the target organs, and thus, providing one or more of the following therapeutic properties attributed to ATX, including: anti-inflammatory activity, antioxidant, anti-aging, anticancer, antibacterial, antithrombotic, free radical scavenger, tissue regeneration, anti neurodegenerative activity and antibacterial properties.

The term "biocompatible" or "biocompatibility" in the context of the polymer of the present disclosure, is denoted as a polymer that has the ability to perform with an appropriate response in a living system (e.g., the body of a mammal) or has ability to be in contact with a living system without producing a reverse response. An appropriate response will determine the clinical success of a medical device, pharmaceutical, drug delivery device, etc.

The term "anti-inflammatory" in the context of the present disclosure, is denoted as the ability of a polymer of the invention to qualitatively or quantitatively reduce inflammation and any of the symptoms derived there from when used in any context by a subject in need thereof.

The term "antioxidant" in the context of the present disclosure, is denoted as the ability of a polymer of the invention to qualitatively or quantitatively inhibits the oxidation of the surrounding environment when used in any context by a subject in need to thereof.

The term "anticancer" or "anti-cytotoxic" in the context of the present disclosure, is denoted as the ability of a polymer of the invention to qualitatively or quantitatively prevent, inhibit, reduce the effect of cytotoxic agents causing abnormal cancerous growth in a subject treated with an element comprising a polymer of the invention.

The term "antibacterial" in the context of the present disclosure, is denoted as the ability of a polymer of the invention to qualitatively or quantitatively prevent, inhibit, reduce bacterial growth or any of its associated symptoms in a subject treated with an element comprising a polymer of the invention.

The term "antithrombotic" in the context of the present disclosure denotes a polymer that has sufficient anticoagulant activity, and thus, qualitatively or quantitatively inhibits, prevents or reduces the coagulation (clotting) of blood. Such polymer can be utilized as an element for use in the treatment of thrombotic disorders, such as medical devices, including but not limited to catheters, dialysis devices, etc. In some embodiments, antithrombogenicity can be provided to a medical device by using the a polymer disclosed herein as a surface coating of a medical device (for example, polymer for use in catheter or catheter coating).

In some embodiments, the polymer disclosed herein is biocompatible. In such embodiments, the biocompatible polymer is biodegradable.

In some embodiments, the polymer described herein having at least one of mechanical stability, microbial stability, chemical stability and any combinations thereof.

A further aim of the invention is to provide an antithrombic medical device having superposed on its surface a polymer as disclosed herein, having a polymerized protein substantially free from at least one of thrombus, fibrin sheath and biofilm. Fibrin is an insoluble protein formed from fibrinogen during clotting of the blood, which forms a fibrous mesh that impedes the flow of blood. At times, the polymerized protein layer or protein is produced by treating a blood plasma-forming protein with a proteolytic enzyme. Thus, in some embodiments, the polymer described herein further comprising a protein. In some embodiments, an element or a device comprising a polymer of the invention provides antifouling effect of the surrounding environment. In one aspect, the invention provides a polymer of the disclosure for use in removal fouling compounds (such as for example proteins).

The polymer described herein can be used in various applications. For instance, use of a polymer disclosed herein for the preparation of a medicament, a medical device, a coating, a thin film, a biofilm, etc.

The present disclosure aims to provide a medical device coated with, associated with or comprising the polymer disclosed herein, for insertion or implantation into the body which will retain anti-infectivity during insertion or implantation, as well as after the device is removed from the body. Such medical device for insertion, implantation or the like into tissue will resist infection, inhibit inflammation and inhibit the growth of tissue around and onto the device. The polymer comprises at least active ATX moieties, wherein these active moieties can be capable of being released over a desired period of time (usually desired for a long duration), once the coated medical device is inserted into the body and comes in contact with body fluids.

Thus, in a further aspect, the present disclosure provides a medical device comprising at least one polymer disclosed herein. In some embodiments the medical device is an implantable medical device (i.e. a medical device that is implanted permanently or temporarily in the human body).

In some embodiments, the medical devices are selected from any one of sutures, wound healing patches, stents, implants, dental implants, orthopedic implants, catheters, valves, tissue engineering scaffolds, soft tissue fillers, bone pins, anti-inflammatory coatings, etc. In some embodiments, the polymer disclosed herein is included in the medical device, e.g., stent, suture, implant, etc, as a coating, such as to provide the medical device with anti-inflammatory, anti-cancerous, anti-bacterial, anti-thrombotic and anti-oxidant properties.

Medical devices used in a living body require affinity for blood, body fluids, or a living tissue.

Thus, in some embodiments, the medical device as disclosed herein, wherein the polymer forms a coating on the surface of the device. In some embodiments, the medical device being resistant to infection.

In further embodiments, the medical device is made of or comprises the polymer disclosed herein, thereby providing a biodegradable medical device that biodegrades over time in a living body while providing the functional activities of the ATX, as detailed above, over a period of time. For instance, a biodegradable implant can be prepared from ATX polymer, possibly together with at least one other biodegradable moiety. Since ATX enhances regeneration of a tissue, such an implant can be utilized, e.g., to replace a tumor removed (fully or partially), thus providing an implant that both biodegrades with time as well as aiding in the regeneration of natural tissue to grow in place of the tumor (or cist, polyp, etc). If such tumor removed is cancerous, such implant comprising the ATX polymer of the invention, having anti-cancerous properties, can also aid in preventing the recurrence of cancer.

The present invention provides, use of a polymer as disclosed herein above and below, for the preparation of a biocompatible element.

In another one of its aspects the invention provides, use of a polymer as disclosed herein above and below, for the preparation of a biocompatible and antibacterial element. In yet another aspect the invention provides use of a polymer as disclosed herein above and below, for the preparation of an element being at least one of biocompatible, antibacterial, anti-infectious, anti-inflammatory, anti-cancerous, antioxidant and antithrombotic. In a further aspect the invention provides use of a polymer, as disclosed herein above and below, for the preparation of an element being at least one of thermally stable, chemically stable, mechanically stable or any combinations thereof.

The invention provides a polymer as disclosed herein above and below for use in the treatment of at least one of inflammation, thrombosis, infection, cancer, and any symptoms associated therewith. The invention provides a polymer as disclosed herein above and below for use in the treatment of at least one of condition associated with an implantable device including, but not limited to inflammation, thrombosis, infection, cancer, and any symptoms associated therewith.

The term "element" as used in the context of the present disclosure refers to any constituent or component of an end product which is used as a whole or being part of a combination of elements or components. In some embodiments, said element is selected from device, part of a device, a medical product, a tool for using in medical procedures and so forth. In some other embodiments, said element being selected from a medical device, surface coating, suture (either biodegradable or biostable), patch, film, biofilm, and so forth.

As appreciated, the polymer disclosed herein inhibits the growth of bacteria on a surface region of an implant. As exhibited in the experimental section, the ability of the bacteria to form a biofilm in the presence of the polymer of the present disclosure was observed after culturing for 24 hours.

In a further aspect, the disclosure provides a method of preventing or inhibiting infections associated with use of an implant, said method comprising treating a surface region of said implant with a polymer disclosed herein. The disclosure further provides a polymer as defined herein above and below (according to general formula I), for use in therapy.

The term "treating" as used herein above means the management and care of a patient for the purpose of combating an infection associated with a surface region of an implant associated with said patient, with the polymer of the invention. The term includes the delaying of the progression of the infection, the alleviation or relief of symptoms and complications, and/or the cure or elimination of the infection. The patient to be treated is preferably a mammal, in particular a human being.

Some embodiments of the invention are directed to a process for preparing polymer based ATX (pATX). Further embodiments are directed to a process for preparing co-pATX. An embodiment of a process for preparing pATX is provided in FIG. 1. An embodiment for the preparation of a hydrophobic co-pATX is provided in FIG. 2 (showing the polymerization of copolymer poly(astaxanthin-co-suberic acid), related to herein as poly(ATX-co-SA)). An embodiment for the preparation of a hydrophilic co-pATX is provided in FIG. 3 (showing the polymerization of copolymer poly(astaxanthin-co-polyethylene glycol), related to herein as poly(ATX-co-PEG)).

According to some embodiments, a catalyst is added to the reaction vessel. According to some embodiments, the catalyst is selected from DPTS (4-(N,N'-Dimethylamino) pyridinium 4-toluenesulfonate), pyridine, 4-dimethylaminopyridine, and proline.

Some embodiment of the invention are directed to a process for preparing pATX comprising:
  mixing ATX, an organic solvent and triethylamine in a dry reaction vessel under $N_2$ or Ar;
  adding oxalyl chloride in an organic solvent to the reaction vessel; optionally adding a catalyst;
  maintaining the reaction vessel in a dark environment; allowing the mixture to react for 1-24 hours; and precipitating the products.

According to some embodiments, the reaction vessel is an amber vessel. According to some embodiments the organic solvent is selected from dichloromethane, chloroform, tetrahydrofuran, dimethylsulfoxide or any other suitable solvent. According to some embodiments a water or acid quencher is added to the reaction vessel. According to some embodiments, the product is precipitated with IPA, ethanol, methanol, water or any other appropriate non-solvent.

Some embodiments of the invention are directed to a process for preparing polyester based co-pATX comprising:
  mixing ATX and diacid or diacyl chloride in equimolar amounts in a reaction vessel that is dry and saturated with $N_2$ or Ar;
  adding an organic solvent to the reaction vessel in a 2-10% w/v ratio; optionally adding a catalyst;
  maintaining the reaction vessel in a dark environment; allowing the mixture to react for 1-24 hours; and precipitating the products.

According to some embodiments, the reaction vessel is an amber vessel.

According to some embodiments the organic solvent is selected from dichloromethane, chloroform, tetrahydrofuran, dimethylsulfoxide or any other suitable solvent. According to some embodiments a water or acid quencher is added to the reaction vessel. According to some embodiments, the product is precipitated with IPA (isopropanol), ethanol, methanol, water or any other appropriate non-solvent.

Some embodiments of the invention are directed to a process for preparing polycarbonate based co-pATX comprising:
- mixing ATX and a diol, phosgene, phosgene derivatives, (bis)chloroformate in equimolar amounts in a reaction vessel that is dry and saturated with $N_2$ or Ar; adding an organic solvent to the reaction vessel in a 2-10% w/v ratio; optionally adding a catalyst;
- maintaining the reaction vessel in a dark environment; allowing the mixture to react for 1-24 hours; precipitating the products.

According to some embodiments, the reaction vessel is an amber vessel. According to some embodiments the organic solvent is selected from dichloromethane, chloroform, tetrahydrofuran, dimethylsulfoxide or any other suitable solvent. According to some embodiments a water or acid quencher is added to the reaction vessel. According to some embodiments, the product is precipitated with IPA, ethanol, methanol, water or any other appropriate non-solvent.

Some embodiments of the invention are directed to a process for preparing polyurethane based co-pATX comprising:
- mixing ATX and a diol and a diisocyanate in equimolar amounts in a reaction vessel that is dry and saturated with $N_2$ or Ar;
- adding an organic solvent to the reaction vessel in a 2-10% w/v ratio; optionally adding a catalyst;
- maintaining the reaction vessel in a dark environment; allowing the mixture to react for 1-24 hours; precipitating the products.

According to some embodiments, the reaction vessel is an amber vessel. According to some embodiments the organic solvent is selected from dichloromethane, chloroform, tetrahydrofuran, dimethylsulfoxide or any other suitable solvent.

According to some embodiments a water or acid quencher is added to the reaction vessel. According to some embodiments, the product is precipitated with IPA, ethanol, methanol, water or any other appropriate non-solvent. According to some embodiments the catalyst is selected from 1,4-diazabicyclo[2.2.2]octane, dimethylcyclohexylamine, dimethylethanolamine.

All amounts or measures indicated below with the term "about" followed by a number should be understood as signifying the indicated number with a possible tolerance between approximately 10% above the indicated number and 10% below that number.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Example 1

Polymerization of Homopolymer Polyastaxanthin (Referred Herein: pATX).

1 mmol ATX, 4 mL DCM, and 2 mmol triethylamine were placed in a 50 mL amber scintillation vial. The vial was placed in ice water (exothermic reaction). 1 mmol oxalyl chloride in 4 mL DCM was added under $N_2$. The reaction vessel was covered with aluminum foil in order to protect the reactants from light, and stirred in the ice water for two hours. To complete the reaction, the reagents were stirred for an additional for 2 h at room temperature. The solution was then precipitated in isopropyl alcohol (IPA). The precipitated product was then collected and dried under vacuum overnight. The reaction yield was calculated from the dry weight of the precipitate. 10 mg were collected and dissolved in THF (2 mL) for molecular weight analysis using gel permeation chromatography (GPC, VISCOTEK equipped with RI and UV detectors using PS standards.). For further analysis, solvent cast films of the polymer were prepared. The remaining polymer powder was dissolved in THF (10% w/v) and after complete dissolution was cast into a polytetrafluoroethylene (PTFE) mold under $N_2$ for 8 hours and then placed in a desiccator for drying overnight.

Figure 1:
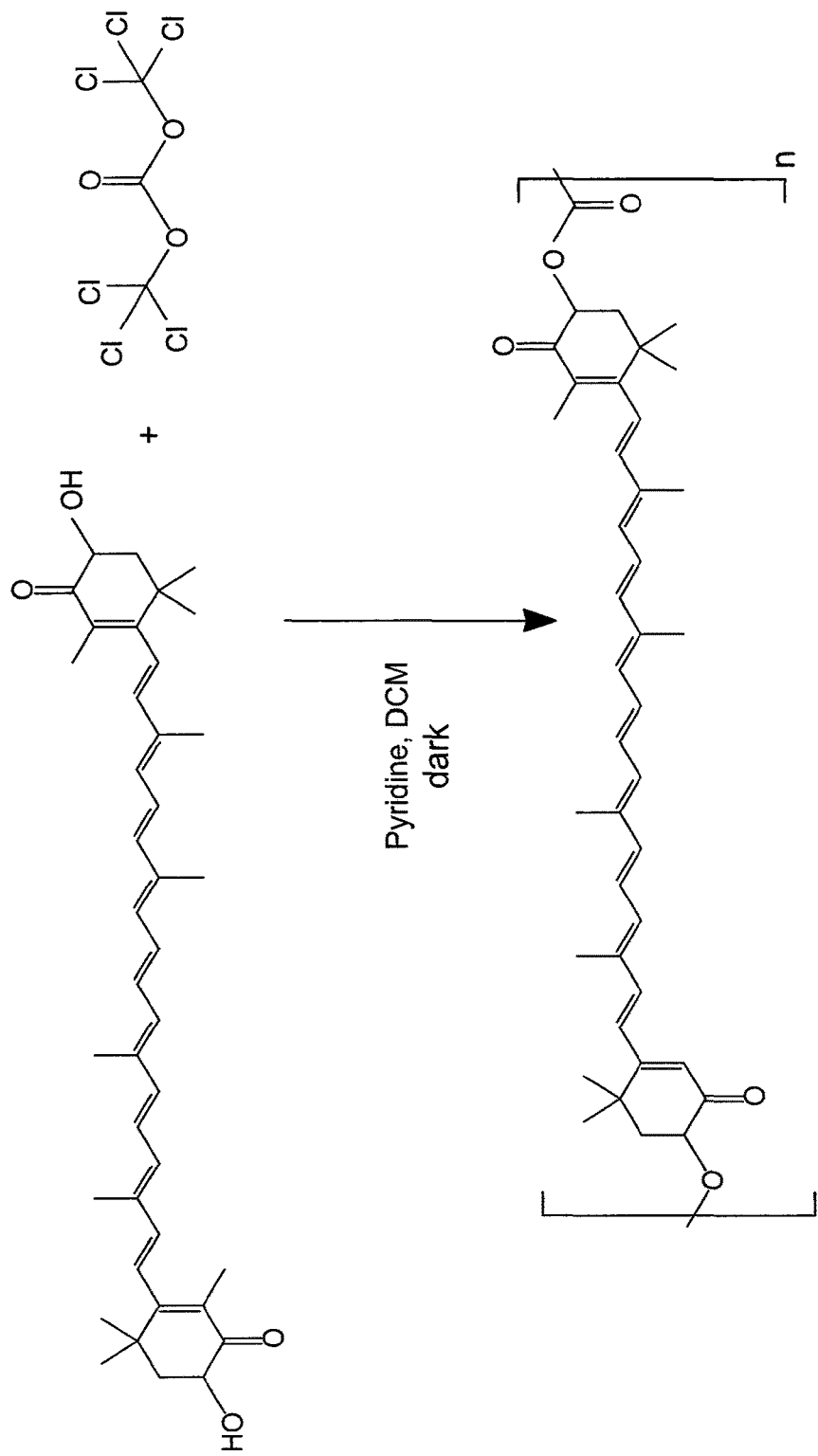
FIG. 1 presents a scheme of a process for preparing ATX homopolymer, referred herein as pATX, according to an embodiment of the invention.
Figure 2:
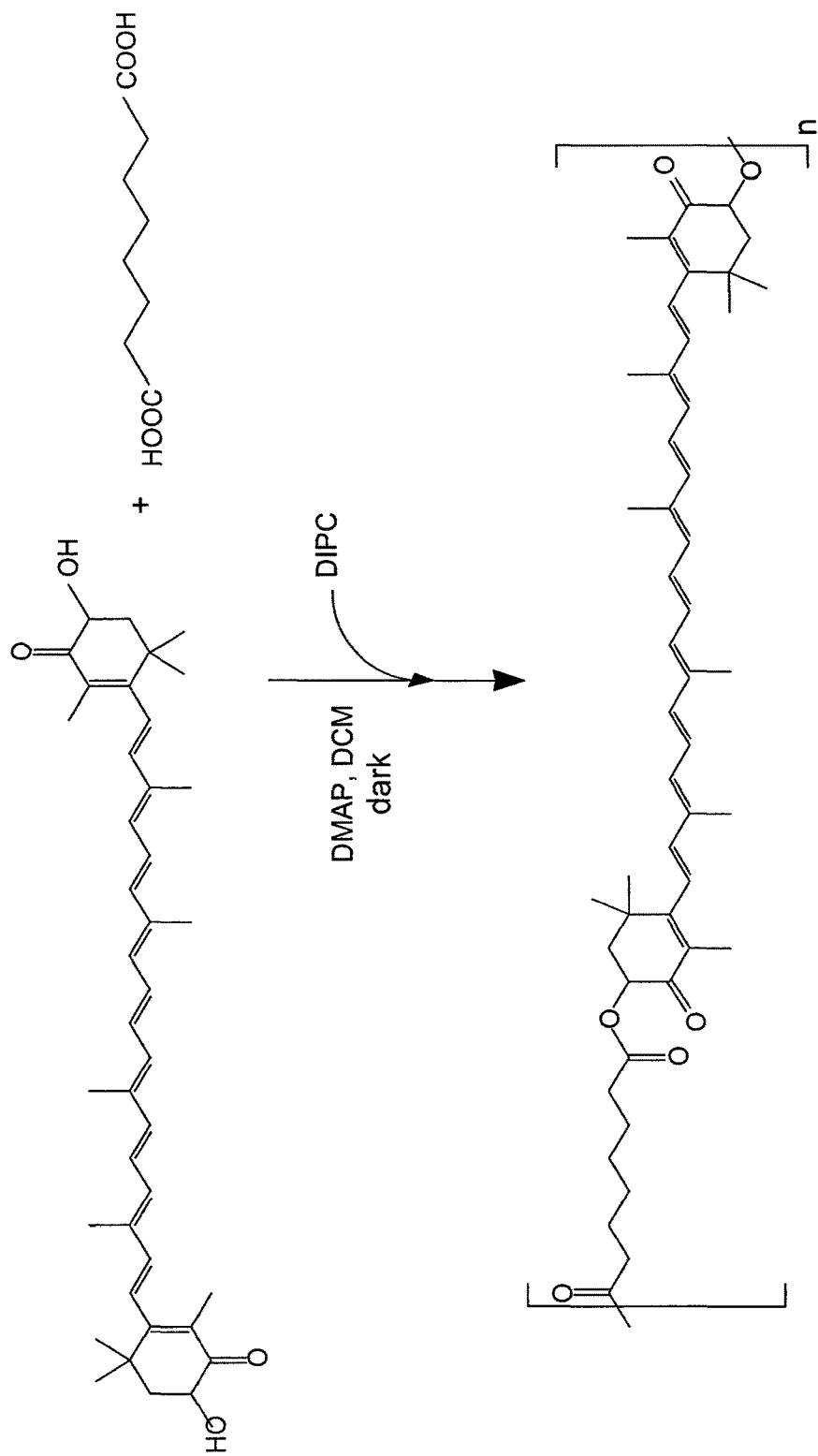
FIG. 2 presents a scheme for the preparation of a hydrophobic ATX co-polymer (showing the polymerization of co-polymer poly(astaxanthin-co-suberic acid) referred herein as poly(ATX-co-SA)), according to an embodiment of the invention.
Figure 3:
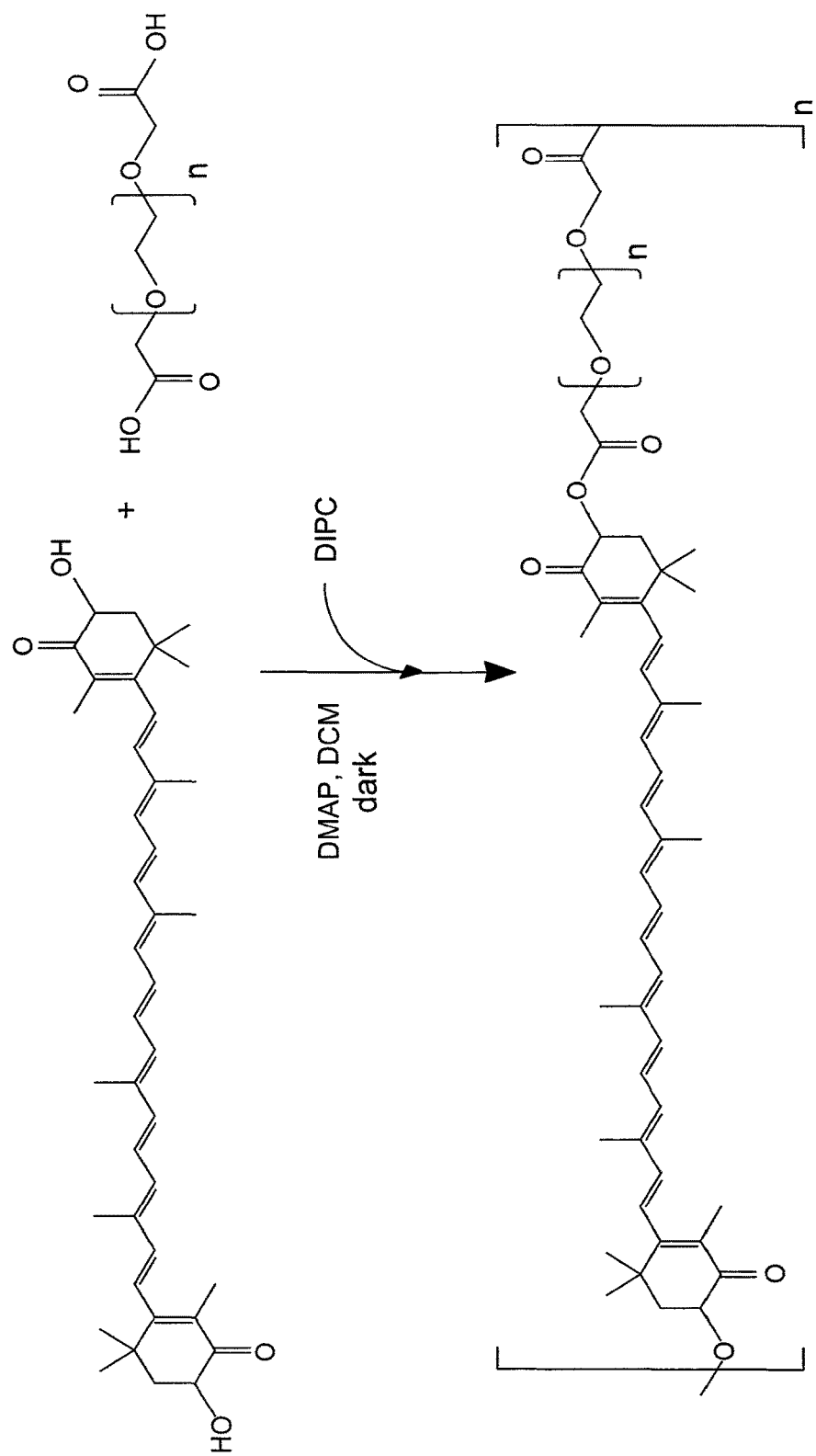
FIG. 3 presents a scheme for the preparation of a hydrophilic ATX co-polymer (showing the polymerization of co-polymer poly(astaxanthin-co-polyethylene glycol) referred herein as poly(ATX-co-PEG)), according to an embodiment of the invention.
Figure 4:
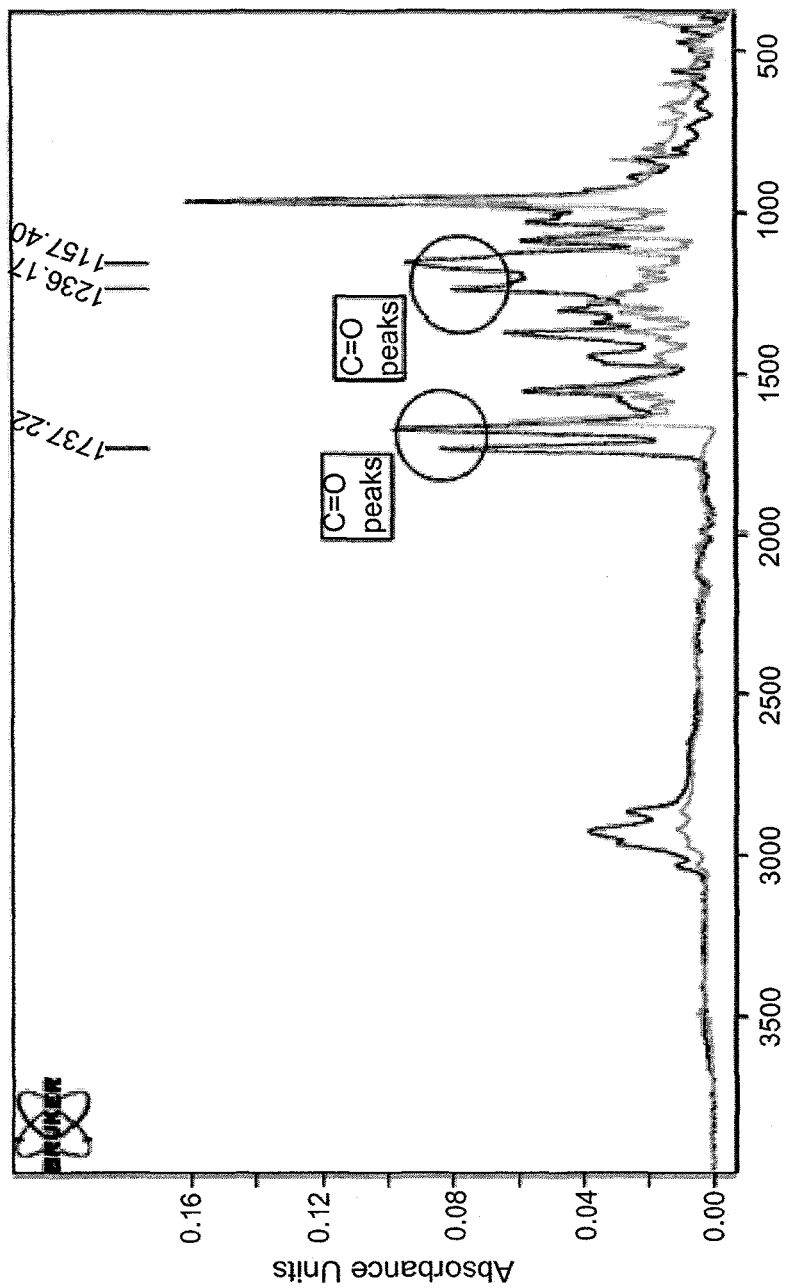
FIG. 4 provides FTIR-ATR analysis of ATX powder and ATX homopolymer, pATX, according to Example 1 of the present invention.

FTIR-ATR analysis of the solid films (recorded on a BRUKER S ALPHA-P, ATR-FTIR) was performed on the prepared films in comparison to ATX powder is displayed in FIG. 4. The formation of ester groups (1737 $cm^{-1}$, 1238 $cm^{-1}$), with the disappearance of hydroxyl group (3500 $cm^{-1}$) are evident to the formation of an ester group within the reaction.

Figure 5:
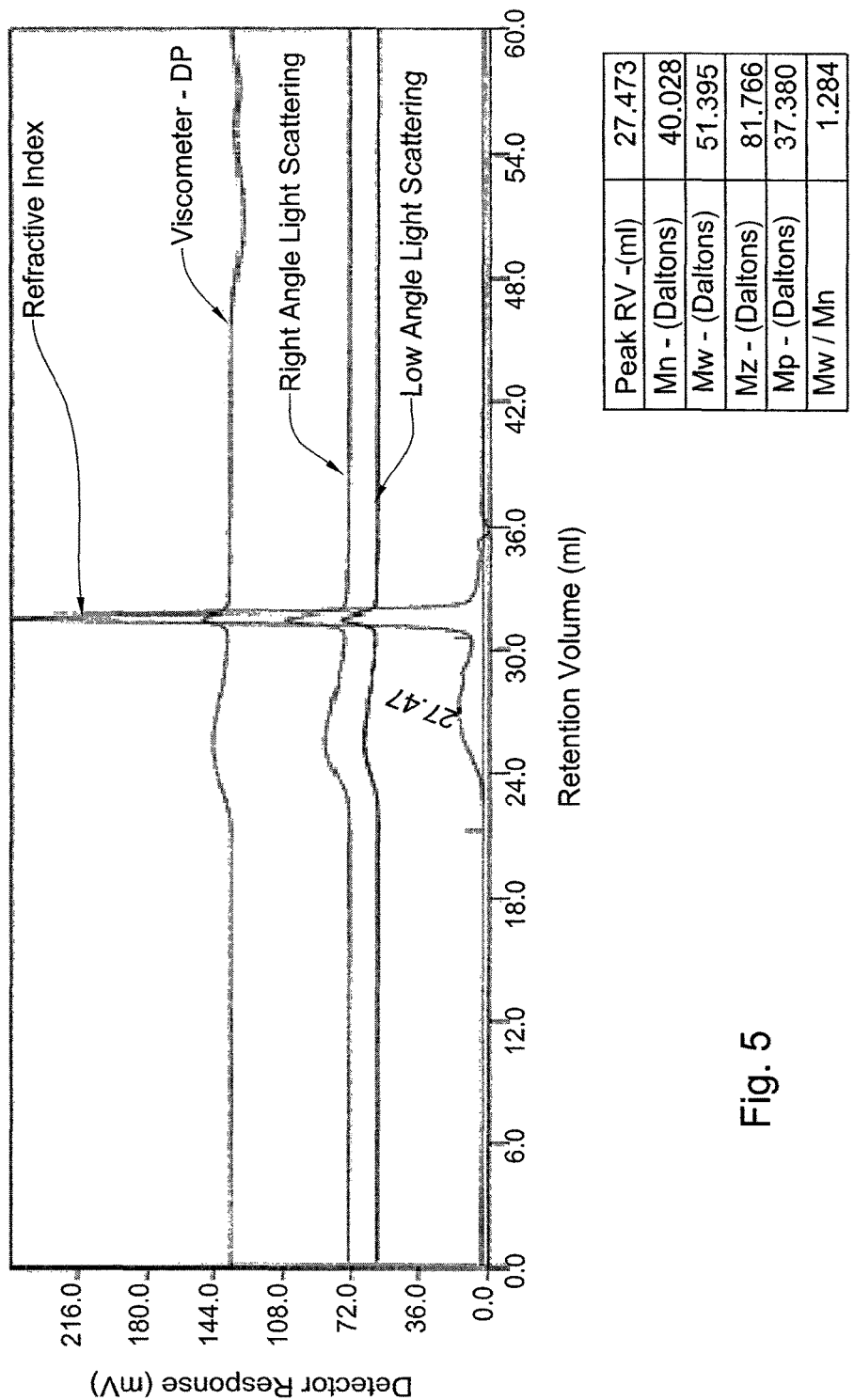
FIG. 5 provides gel permeation chromatography (GPC) results of the ATX homopolymer, pATX, according to Example 1 of the present invention.

The average molecular weight of the pATX polymer of Example 1 was evaluated by gel permeation chromatography (GPC) analysis and displayed in FIG. 5. The formation of a high molecular weight polymer was confirmed, where a polymer with weight average molecular weight of 47 kDa with a polydispersity index (PDI) of 1.4 was obtained.

Example 2

Polymerization of Copolymer Poly(Astaxanthin-Co-Suberic Acid) [Referred Herein: Poly(ATX-Co-SA)]

1.0 mmol ATX and 1.0 mmol suberic acid were placed in a dry 50 ml amber scintillation vial. 20 ml of dry dichloromethane were added and stirred under $N_2$ until complete dissolution. 0.5 mmol of 4-dimethylaminopyridin (DMAP) was added followed by 6 mmol of carbodiimide (DIC) over a 3 hour period (various carbodiimide derivatives can be used). The reaction vessel was covered with aluminum foil and stirred overnight. Precipitation was performed using isopropanol. The precipitated product was then collected and dried under vacuum overnight. The reaction yield was calculated from the dry weight of the precipitate. 10 mg were collected and dissolved in THF (2 mL) for molecular weight analysis using gel permeation chromatography (GPC). For further analysis, solvent cast films of the polymer were prepared. The remaining polymer powder was dissolved in THF (10% w/v) and after complete dissolution, cast into a PTFE mold under $N_2$ for 8 hours and then placed in a desiccator for drying overnight.

Figure 6:
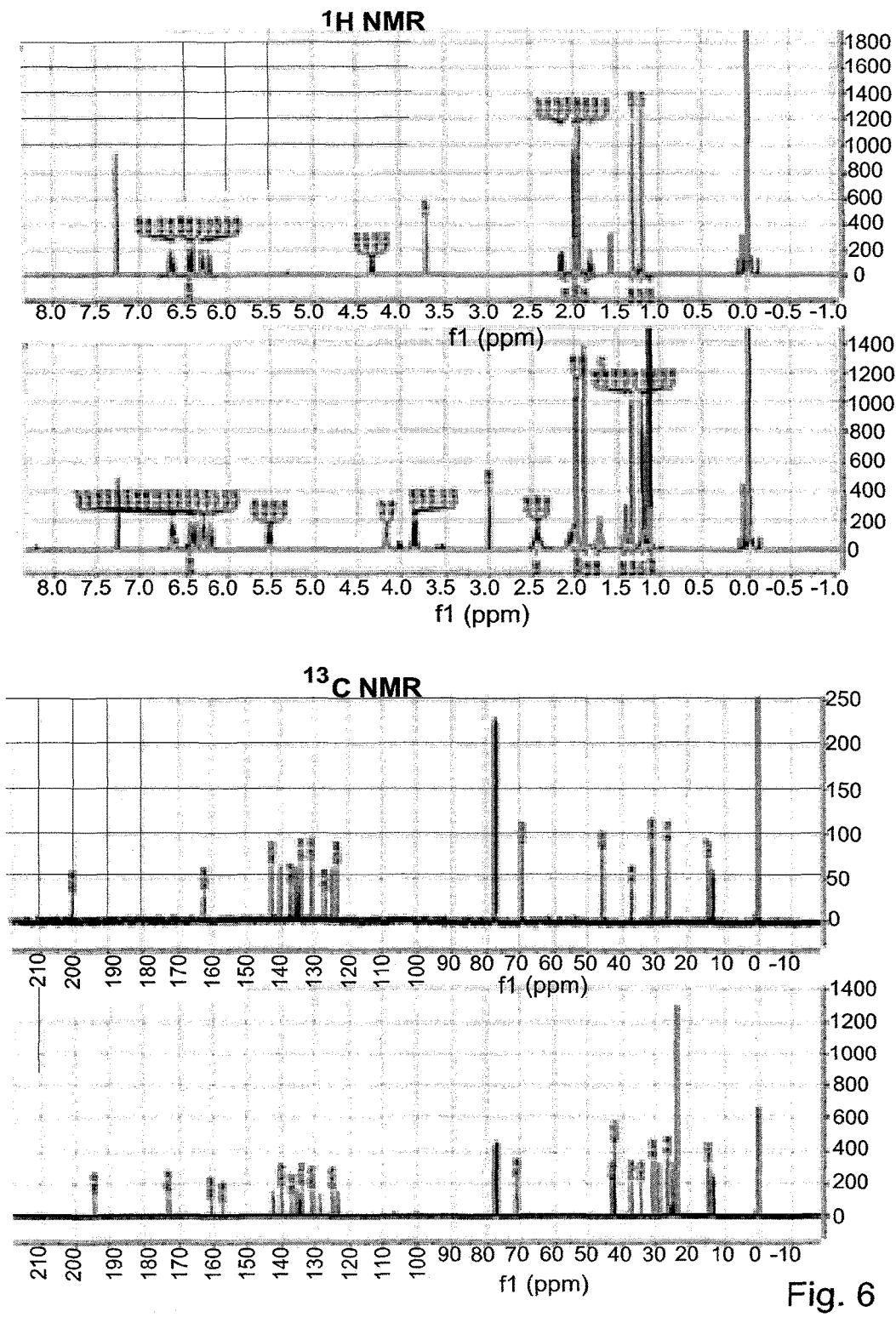
FIG. 6 provides NMR analysis of ATX powder and the ATX polymer, poly(ATX-co-SA), according to Example 2 of the present invention.
Figure 6:
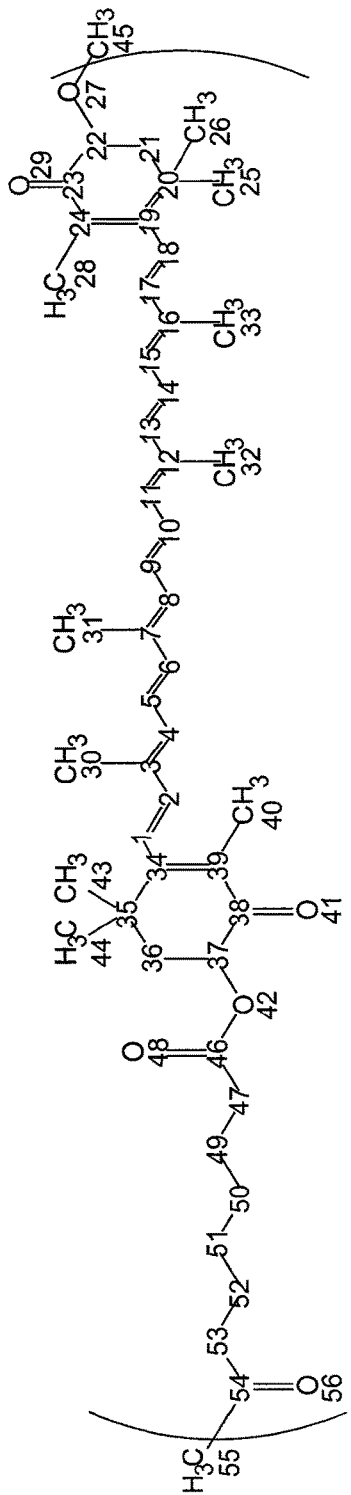

The results of FTIR-ATR analysis performed on the prepared films of the poly(ATX-co-SA) of Example 2 is displayed in FIG. 6. The formation of ester groups (1735 $cm^{-1}$) is evident to the formation of a polyester within the reaction.

Figure 7:
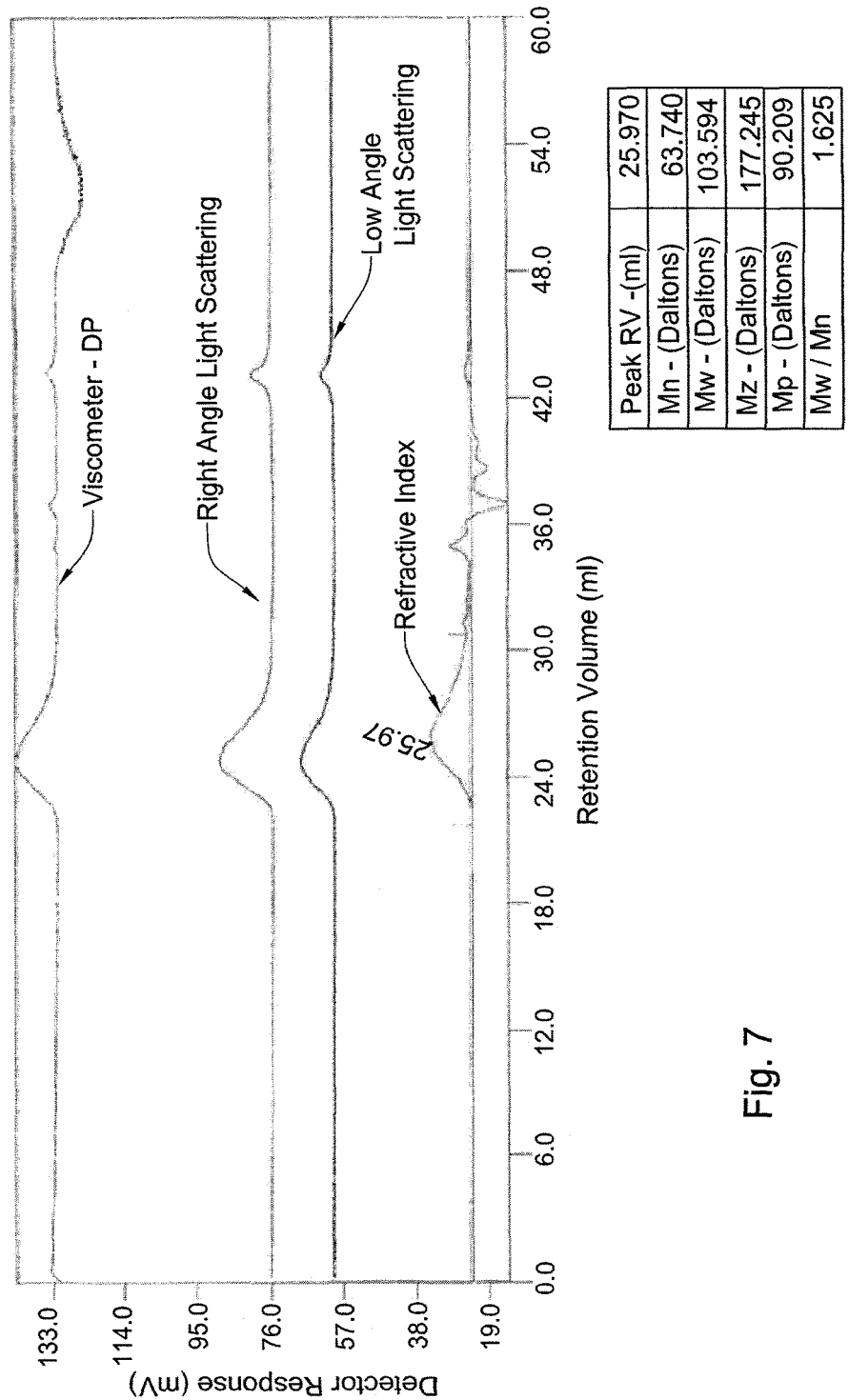
FIG. 7 provides gel permeation chromatography (GPC) results of the ATX polymer, poly(ATX-co-SA), according to Example 2 of the present invention.

The successful synthesis of a high molecular weight polymer poly(ATX-co-SA) of Example 2 was confirmed through GPC analysis, where a polymer with average molecular weight of 103.5 kDa with a PDI of 1.6 was obtained (shown in FIG. 7).

Figure 8:
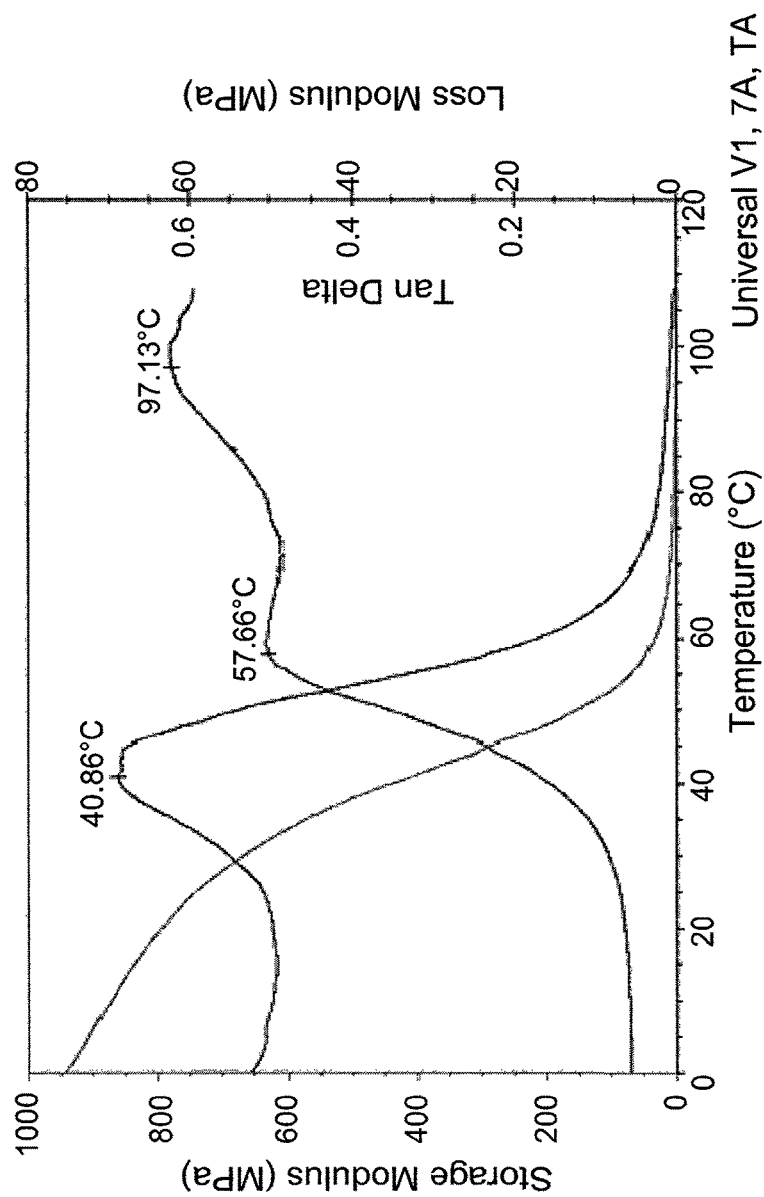
FIG. 8 provides DMA results of the ATX polymer, poly(ATX-co-SA), according to Example 2 of the present invention.

A dynamic mechanical analysis (DMA) of the obtained poly(ATX-co-SA) sample, using a TA Q800 DMA operated at a temperature range of −30° C. to 120° C., indicated that the glass transition temperature of the resulting polymer is 60° C., as illustrated in FIG. 8.

A differential scanning calorimetry (DSC) analysis of the same material resulted in Tg of approximately 50° C.

The cast poly(ATX-co-SA) films have a green metallic color, possibly due to the presence of many conjugated double bonds in the polymer. A film sample was tested according o the Van der Pauw method (ASTM F76). The resulting surface resistivity was 7.084 MΩ/sq, indicating a possibly inherently electrically dissipative polymer.

For evaluation of the biodegradation potential, poly(ATX-co-SA) film samples were incubated at 37° C. in phosphate buffer saline with pH of 7.4 for 1, 3, 7, 14 & 30 days. Control samples were kept under vacuum at 0° C. Within 30 days, a 5% mass loss was observed. GPC analysis indicated a molecular weight loss of 60% indicating a potentially bulk erosion mechanisms, where the loss of polymer Mw precedes mass loss.

Some experiments were conducted using DPTS (4-(N,N'-Dimethylamino) pyridinium 4-toluenesulfonate) as a catalyst, which was added to the reaction vessel after dissolution, before the addition of the carbodiimide.

Example 3

Polymerization of Copolymer Poly(Astaxanthin-Co-Polyethylene Glycol) [Referred Herein: Poly(ATX-Co-PEG)]

5.75 mmol of DIC were added over 3 hrs, under $N_2$ to a reaction vessel containing 1 mmol ATX, 1 mmol poly (ethylene glycol) bis(carboxymethyl) ether, and 14 mL DCM, to allow a controlled polymerization rate and to obtain high molecular weight polymers. The reaction vessel was covered with aluminum foil and stirred for additional 3 hrs to reach high molecular weight polymers. The solution was then precipitated in IPA. The precipitated product was then collected and dried under vacuum overnight. The reaction yield was calculated from the dry weight of the precipitate. 10 mg were collected and dissolved in THF (2 mL) for molecular weight analysis using gel permeation chromatography (GPC). For further analysis, solvent cast of the poly(ATX-co-PEG) films were prepared. The remaining poly(ATX-co-PEG) powder was dissolved in THF (10% w/v) and after complete dissolution, was cast into a PTFE mold under $N_2$ for 8 hours and then placed in a desiccator for drying overnight.

Figure 9:
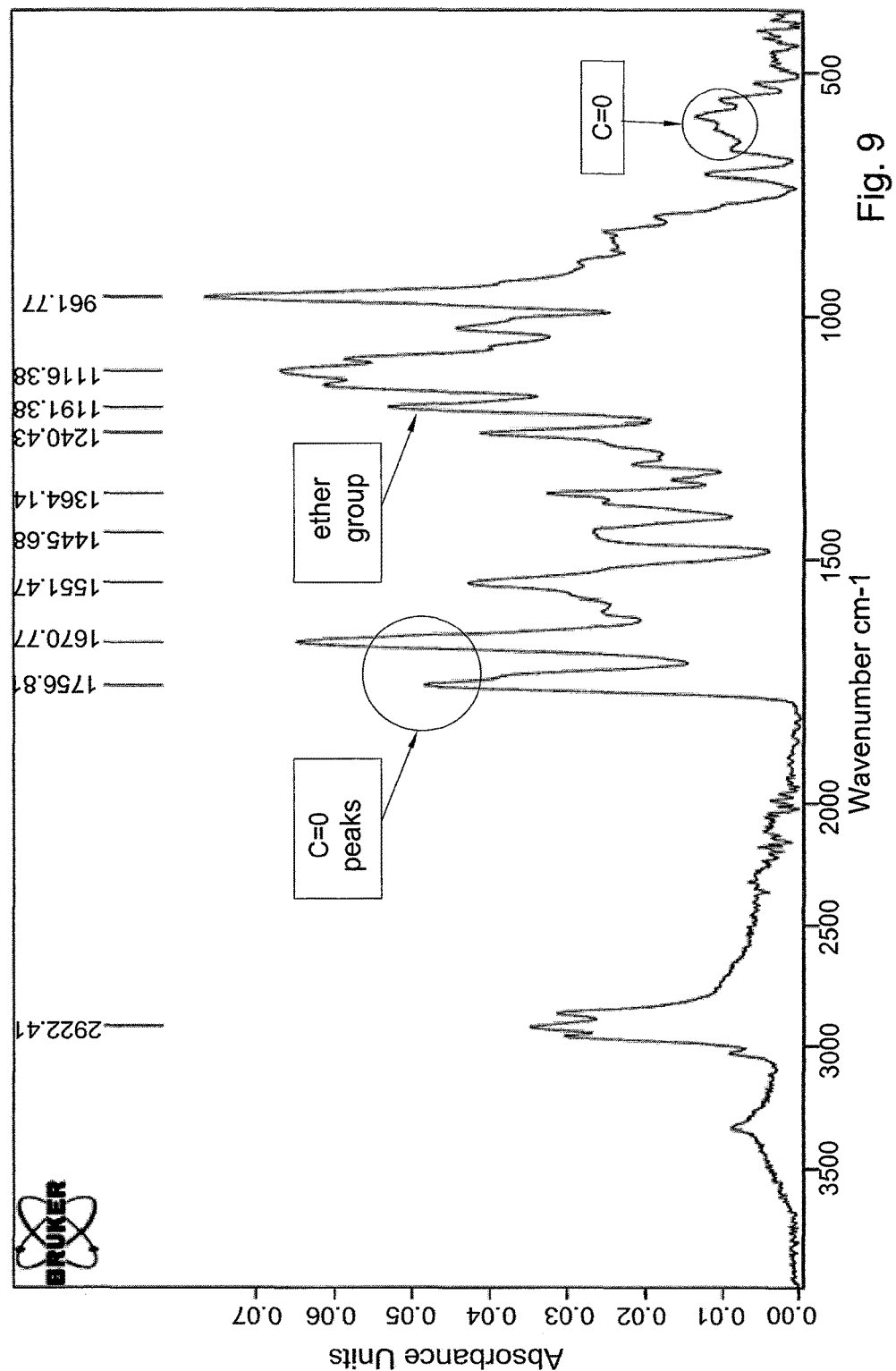
FIG. 9 provides FTIR-ATR analysis of the ATX polymer, poly(ATX-co-PEG), according to Example 3 of the present invention.

FTIR-ATR analysis performed on the poly(ATX-co-PEG) films prepared according to Example 3 is shown in FIG. 9. The formation of ester groups (1756 $cm^{-1}$) and ether groups derived from the PEG (1240 $cm^{-1}$) are evident to the formation of a polyester within the reaction.

Figure 10:
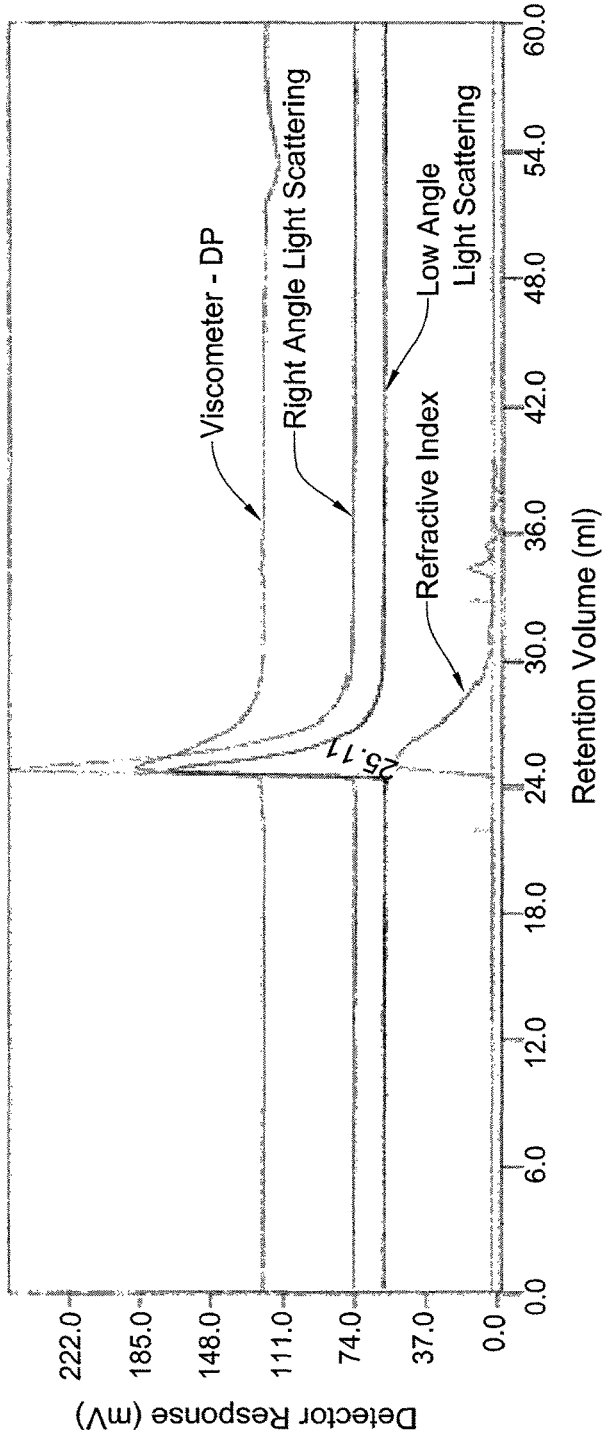
FIG. 10 provides gel permeation chromatography (GPC) results of the ATX polymer, poly(ATX-co-PEG), according to Example 3 of the present invention.

The successful synthesis of a high molecular weight polymer was confirmed through GPC analysis (exhibited in FIG. 10), where a polymer with weight average molecular weight of 45 kDa with a PDI of 1.7 was obtained.

Figure 11:
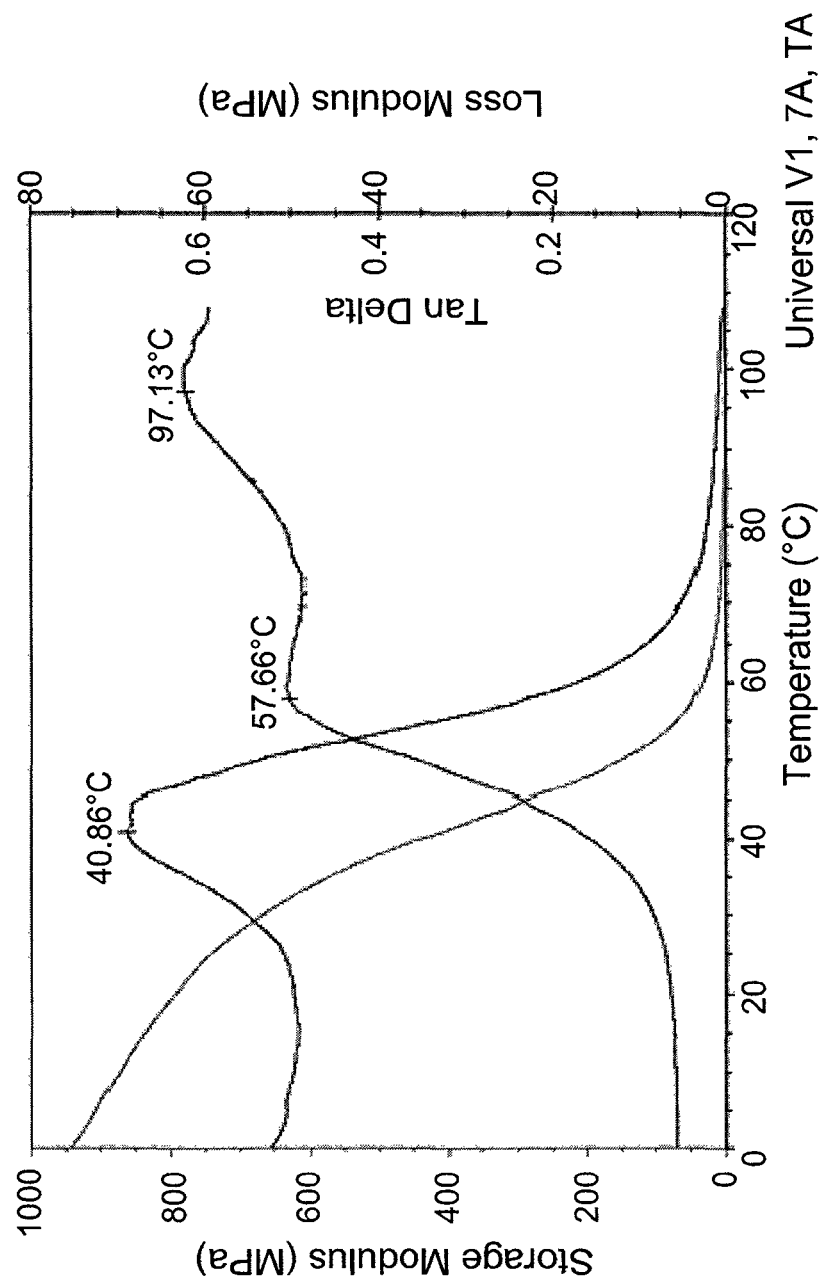
FIG. 11 provides DMA results of the ATX polymer, poly(ATX-co-PEG), according to Example 3 of the present invention.

A dynamic mechanical analysis (DMA) of the obtained poly(ATX-co-PEG) of Example 3 indicated that the glass transition temperature of the resulting polymer was 41° C., as illustrated in FIG. 11.

A differential scanning calorimetry (DSC) analysis of the same material resulted in Tg data of approximately 45° C.

The cast poly(ATX-co-PEG) films of Example 3 have a green metallic color, possibly due to the presence of many conjugated double bonds in the polymer. Degradation studies in phosphate buffer saline revealed a molecular weight loss of over 50% in four weeks, and mass loss of 20%.

Table 1 lists some of the polymers provided according to the present disclosure. The different polymers were prepared by using varying comonomers. A wide range of thermal and mechanical properties was achieved as exhibited in the table. The Mw ranged from 19.4 kDa for the poly(ATX-co-dodecandioic acid), while the poly(ATX-co-suberic acid) exhibited a higher Mw of 103.5 kDa. The structure of the various polymers obtained was determined by NMR. NMR spectra were recorded on a Varian NMRS 300 or 500 MHz instrument. $^1$H NMR chemical shifts are reported in ppm relative to the solvent's residual $^1$H signal. $^{13}$C NMR spectra were recorded at 125 MHz.

Without being bound by theory, it is believed that the nature of the comonomer alters the polymer's properties. As shown in Table 1, the mechanical property varies as a function of the different monomeric unit that composes the polymer, for example, the Young's modulus ranges from 200 to 900 MPa for the different polymers comprising different monomeric units.

Thus, it is believed that the polymers disclosed herein can be fabricated into various shapes and forms using conventional techniques, and can be applied as coating for various medical devices.

TABLE 1

Properties and structure of the polymers provided according to the invention.

| Polymer | MW (Da) | Tg (° C.) (DMA) | Young's Modulus (MPa) | Structure (Confirmed by NMR) |
|---|---|---|---|---|
| Poly(ATX-co-suberic acid) | 103,500 | 68 | 900 | |
| Poly(ATX-co-sebacic acid) | 31,400 | 54 | 830 | |
| Poly(ATX-co-dodecanedioic acid) | 19,400 | 39 | 365 | |

TABLE 1-continued

Properties and structure of the polymers provided according to the invention.

| Polymer | MW (Da) | Tg (° C.) (DMA) | Young's Modulus (MPa) | Structure (Confirmed by NMR) |
|---|---|---|---|---|
| Poly(ATX-co-hexadecanedioic acid) | 23,000 | 22 | 125 | |
| Poly(ATX-co-ethylene glycol) | 45,000 | 41 | | |
| Poly(ATX-co-oxalyl chloride) | 51,400 | | | |

Example 4

Antibacterial Tests of the Polymers of the Invention

The potential antibacterial properties of polymer based ATX samples were tested against *Staphylococcus aureus* MRSA252, *S. aureus* MSSA476 and *S. epidermidis* 1457. Using solvent casting method [J. Ghosh et al., *Polymer*, vol. 52, pp. 2.2011, 650-2660], 96 well plates were coated with the following samples—ATX only, ATX+sebacic acid (SA), ATX+Hexadecanoic acid (HA) and ATX+sebacic acid+2% polyethylene glycol (PEG). Each sample coated 3 wells per row and the last row was left blank as a control.

3 ml Trypticase Soy Broth was inoculated with a colony from an overnight plate. Pre-cultures were grown at 37° C. with shaking to mid-exponential phase (2-3 h), and then used to inoculate fresh TSB to a starting $OD_{600}$ of 0.01. 200 μl aliquots of this suspension were then inoculated into wells of one full row of the test plate. The plate was then incubated in a FLUOstar OPTIMA microplate reader at 37° C., and the optical density of each well measured every hour over a 24 h period. After 24 h the suspension in each plate was removed. The plate itself was washed three times with phosphate buffered saline, pH 7.4 (PBS), air dried and stained with 150 μl crystal violet solution. The dye bound to any attached cells was solubilized by addition of 150 μl of 95% ethanol.

Optical density was measured as absorbance at 570 nm using a FLUOstar OPTIMA microplate reader and biofilm positive defined as $OD_{570}$ above 1. All *S. aureus* and *S. epidermidis* isolates were tested in triplicate in three independent experiments. Each plate also consisted of negative controls (wells without bacterial inoculation). Data was analyzed using unpaired t-tests or one-way ANOVA, and the level of significance set at $p<0.05$. The ability of the bacteria to form a biofilm in the presence of the ATX samples was determined after culturing for 24 h using a semi-quantitative biofilm assay.

Figure 12A:
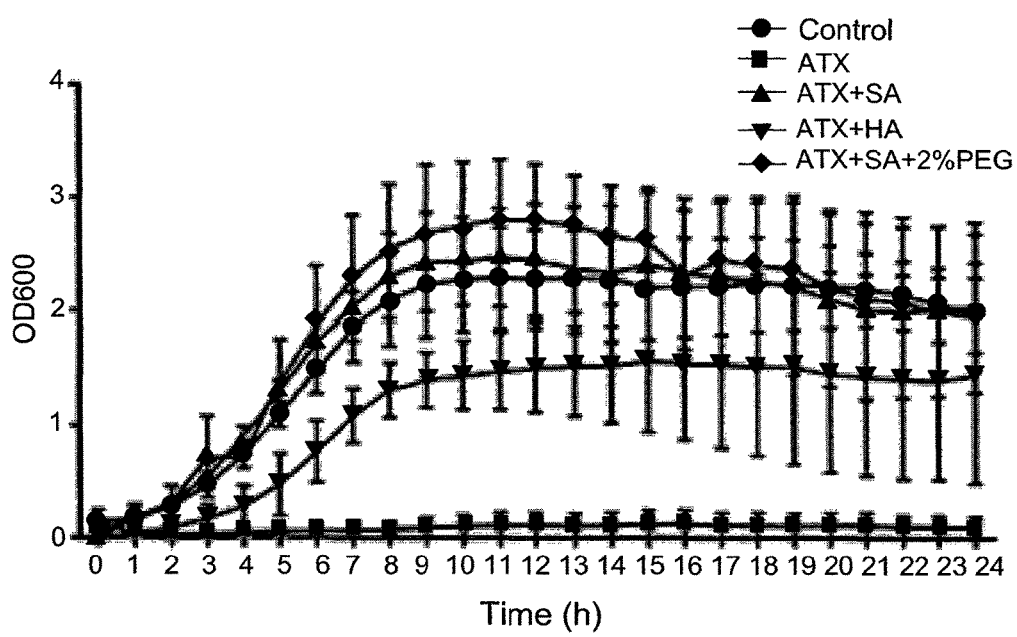
FIG. 12 provides optical density (OD) measurements over 24 hours of inoculated ATX samples, wherein OD570—refers to the optical density at 570 nm and the error bars indicate standard error of mean.
Figure 12B:
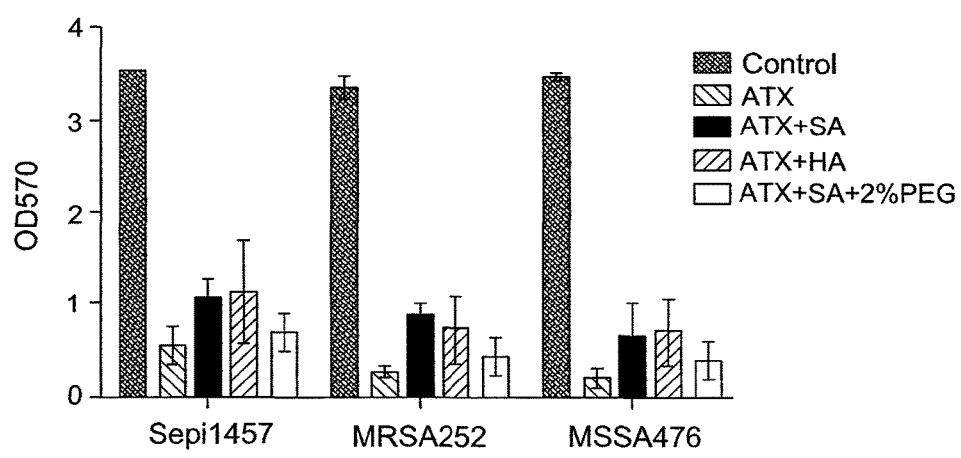

FIG. 12A shows the effect of the ATX samples on the growth of *S. epidermidis* 1457 over the course of 24 h. similar results were obtained with *S. aureus* MRSA252 and *S. aureus* MSSA476. The figure shows that ATX alone has a significant effect on inhibiting the growth of the bacteria, and suggests that some ATX polymer samples have a similar potential. FIG. 12B shows that ATX samples inhibited the bacteria from forming biofilm on assayed ATX and ATX polymer surfaces in comparison to the control ($p\leq 0.005$).

Recent preliminary studies performed under JIS Z 2801 standard and using *S. epidermidis*, have confirmed our reported results of the ATX polymer bacteriostatic nature. In addition, these studies show that the ATX polymer is potentially bacteriocidal (not shown). These results suggest that these ATX polymer samples are bacteriostatic in nature and that further optimized copolymers may have a greater bacteriostatic and bacteriocidal activity. In vitro biodegradation studies indicate that the pATX can become biodegradable polymers, with different erosion mechanism (bulk/surface) as function of hydrophobicity of comonomer. This property may be used as a slow release mechanism of the ATX active constituent. Moreover, Such ATX-based polymers are high Mw plastics that can be molded into various shapes and forms. The ATX polymer can be easily applied as a coating for catheters and other medical device, to provide them with the much needed antimicrobial and hemocompatible properties.

Thus, ATX polymer has the capacity to be tailored towards the localized controlled release of ATX from their polymer form, and/or as bioactive polymers. These intrinsically bioactive materials have the potential to provide antibacterial activity, and anti-thrombotic activity, in addition to anti-oxidative, anti-inflammatory and anti-cancerous properties; and can be used as coatings for medical device and/or modeled as medical device.

thereof.

The invention claimed is:

1. A polymer having a repeating unit comprising at least one astaxanthin moiety, wherein the polymer has the following repeating unit -[ATX]n- wherein ATX is an astaxanthin moiety and n is at least 2, and wherein the polymer has a MW of at least 15 kD.

2. The polymer according to claim 1, wherein the repeating unit further comprises at least one other moiety selected from a bioactive moiety, a biocompatible moiety, hydrophobic moiety, hydrophilic moiety, or any combinations thereof.

3. The polymer according to claim 1, wherein the repeating unit further comprises at least one other moiety selected from a carboxylic acid moiety, an anhydride moiety, an epoxide moiety, an acyl moiety, a phosgene derivative, an isocyanate moiety or any combinations thereof.

4. The polymer according to claim 1, having a MW of between about 15 kDa to about 50 kDa.

5. The polymer according to claim 1, capable of controllably releasing ATX.

6. The polymer according to claim 1, capable of adsorbing at least one protein.

7. The polymer according to claim 1, being at least one of biocompatible, antibacterial, antioxidant, anti-infectious, anti-inflammatory, antithrombotic or any combination thereof.

8. The polymer according to claim 1, being at least one of thermally and mechanically stable.

9. The medical device comprising at least one polymer according to claim 1.

10. The medical device according to claim 9, being an implantable medical device.

11. The medical device according to claim 9, selected from at least one of catheter, valve, stent, scaffold, tissue filler, and wound healing patch.

12. The medical device according to claim 9, wherein said polymer forms a coating on the surface of said device.

13. The medical device according to claim 9, being resistant to infection.

14. The method of inhibiting infections associated with use of an implant, said method comprising treating a surface region of said implant with a polymer according to claim 1.

* * * * *